(12) United States Patent
Björklund et al.

(10) Patent No.: US 11,485,989 B2
(45) Date of Patent: *Nov. 1, 2022

(54) METHOD FOR COOLING AND DETOXIFYING BIOMASS

(71) Applicant: Valmet AB, Sundsvall (SE)

(72) Inventors: Peter Björklund, Umeå (SE); Andreas Averheim, Sundsvall (SE)

(73) Assignee: VALMET AB, Sundsvall (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/952,310

(22) Filed: Nov. 19, 2020

(65) Prior Publication Data

US 2021/0207185 A1 Jul. 8, 2021

(30) Foreign Application Priority Data

Jan. 8, 2020 (EP) .................................... 20150723

(51) Int. Cl.

| | |
|---|---|
| *D21C 3/24* | (2006.01) |
| *D21C 7/00* | (2006.01) |
| *D21C 5/00* | (2006.01) |
| *C12P 19/00* | (2006.01) |
| *C12P 19/14* | (2006.01) |
| *C12P 19/02* | (2006.01) |
| *C13K 1/02* | (2006.01) |
| *D21C 7/06* | (2006.01) |
| *D21C 7/08* | (2006.01) |
| *D21C 7/10* | (2006.01) |

(52) U.S. Cl.
CPC ............... *C12P 19/14* (2013.01); *C12P 19/02* (2013.01); *C13K 1/02* (2013.01); *D21C 5/005* (2013.01); *D21C 7/06* (2013.01); *D21C 7/08* (2013.01); *D21C 7/10* (2013.01)

(58) Field of Classification Search
CPC .. C12P 19/14; C13K 1/02; D21C 7/06; D21C 5/005; D21C 7/00
See application file for complete search history.

(56) References Cited

U.S. PATENT DOCUMENTS

| | | |
|---|---|---|
| 2009/0098616 A1 | 4/2009 | Burke et al. |
| 2009/0098617 A1 | 4/2009 | Burke et al. |
| 2012/0111515 A1 | 5/2012 | Nilsen et al. |
| 2012/0115200 A1 | 5/2012 | Dottori et al. |
| 2016/0069020 A1 | 3/2016 | Dottori et al. |
| 2018/0355303 A1 | 12/2018 | Rowland et al. |
| 2019/0194697 A1 | 6/2019 | Dechman et al. |
| 2021/0340487 A1 * | 11/2021 | Pettersson ............... C12P 19/02 |

OTHER PUBLICATIONS

Extended European Search Report for European Application No. 20150733.2 dated Jul. 16, 2020 (6 pages).
Extended European Search Report for European Application No. 20150723.3 dated Aug. 28, 2020 (7 pages).

* cited by examiner

*Primary Examiner* — Maryam Monshipouri
(74) *Attorney, Agent, or Firm* — Morgan, Lewis & Bockius LLP (57) ABSTRACT

The present invention relates to an improved method and device for treating biomass in which thermally treated biomass is discharged from a pressurized reactor and introduced into a blow tank, wherein the absolute pressure in the blow tank is maintained below atmospheric pressure. The slurry of biomass separated in the blow tank is then enzymatically treated.

16 Claims, 3 Drawing Sheets

METHOD FOR COOLING AND DETOXIFYING BIOMASS

FIELD OF THE INVENTION

The present invention relates to a method and a device for treating hydrolyzed biomass in which thermally treated biomass is discharged from a pressurized hydrolysis reactor into a blow tank, wherein the absolute pressure is maintained below atmospheric pressure. The hydrolyzed biomass is cooled and detoxified by flash evaporation to a temperature suitable for further treatment with for example enzymes.

BACKGROUND ART

It is known in the art to pre-hydrolyse biomass sugars in a reactor in which hemicellulose sugars are dissolved from biomass at elevated temperature and pressure, optionally in the presence of an acidic catalyst. With biomass is here meant any type of lignocellulosic material which contains hydrolysable hemicellulose or cellulose sugars. The biomass is heated with saturated or superheated steam and the temperature in the reactor is typically around 200° C. and the pressure is in the range 15 to 20 bar. There is no free liquid level in the reactor, but the biomass comprises a certain amount of moisture. The biomass is discharged from the reactor after completed sugar hydrolysis to an atmospheric receiving container, in the following called a "blow tank". The temperature of the discharge, which contains mainly biomass, hydrolyzed sugar and water, drops rapidly to about 100° C. when water and other volatile compounds evaporate to equilibrium at the pressure prevailing in the blow tank. Said pre-hydrolyzed biomass is then enzymatically hydrolyzed to release cellulosic sugars. The released sugars are fermented to ethanol or used as feed stock for various chemicals.

The pre-hydrolyzed biomass must be cooled to low temperature and it must be diluted typically to about 40-60° C. and to 10-20% insoluble material content to secure a good enzymatic activity in downstream hydrolysis steps. It is known in the art to cool and dilute hydrolyzed biomass by mixing it with a cold or cooled coolant for example water, recycled process condensate or recycle process filtrate. Additionally, the pH of the pre-hydrolyzed slurry must be adjusted to a pH range 4.0 to 6.5 for optimum enzymatic activity.

Said method of cooling by mixing coolant to the pre-hydrolyzed biomass may result in dilution of the slurry below 15%, which has the drawback of suboptimal conditions with high operation cost because the dilution liquid will be removed in downstream process stages. In addition, the diluted slurry contains carboxylic acids and furfural, which are toxic and may reduce activity of enzymes and yeast in the enzymatic hydrolysis and fermentation steps.

EP 18 208 026.7 discloses a method for treating biomass in which thermally treated biomass is discharged from a pressurized pre-hydrolysis reactor unit and dewatered followed by cooling of the separated liquid phase. Said invention teaches to install a dewatering press or alike to separate hot hydrolysate before cooling it with a heat exchanger. The cooled hydrolysate is then back-mixed with the dewatered biomass which is pumped to enzymatic hydrolysis. The inventors claim that problems with scaling and plugging of cooling heat-exchangers may be reduced with their invention.

US 2015/0232902 A1 describes a method of cooling a thermally hydrolyzed biomass prior to mixing it with enzymes. Said patent teach to split the enzymatic hydrolysis in two steps such that the first enzymatic hydrolysis step operates with a shortened duration (small reactor volume) and the second enzymatic step(s) operates with long duration (large reaction volume) to provide completed saccharification. The duration of the first reactor is such that it saccharifies (liquefies) cellulose enough to provide a pumpable water (hydrolysate) solution through a recycle cooler (heat exchanger). This way it is no longer necessary to recycle coolant (hydrolysate) over the second enzymatic step. The inventors claim that the total (first and second) reaction volume is much smaller in comparison to having only one enzymatic reaction volume. However, said application is still proposing cooling of hot hydrolysate by a recycling process.

EP 3212764 B1 discloses a method for treating biomass and organic waste in which the biomass is discharged from a pressurized pre-hydrolysis reactor by steam explosion into one or more pressure relief tank(s), in which the pressure is reduced from 5-35 bar to atmospheric pressure. The discharged biomass has a temperature of 95-110° C. and is processed to ethanol, hydrogen, lactic acid, methane organic acids or other desired produced by fermentation at a pH of 7-8.5.

There is still a need for an improved method and device for cooling thermally treating biomass to a temperature range of optimum enzymatic activity, which is typically about 40 to 60° C., which avoids diluting the thermally treating biomass with a cooling liquid. Additionally, the problems of adjusting the pH to the pH range of optimum enzymatic activity of 4.0 to 6.5, without further diluting the thermally treating biomass and the presence of toxic components like carboxylic acids and furfural in the pretreated biomass slurry are not solved.

SUMMARY OF THE INVENTION

The present invention relates to a method for treating biomass comprising the steps of
(a) feeding lignocellulosic biomass to a pressurized reactor;
(b) supplying steam to the pressurized reactor and at least partially condensing said steam in the pressurized reactor;
(c) hydrolysing hemicellulose sugars of said biomass with said at least partially condensed steam in the pressurized reactor;
(d) discharging said hydrolyzed biomass from the pressurized reactor into a blow tank by steam explosion to produce steam exploded biomass;
(e) diluting the steam exploded biomass in the blow tank with an aqueous diluent to a pumpable slurry; discharging the pumpable slurry from the blow tank as discharged pumpable slurry stream;
(f) treating the discharged pumpable slurry stream with an enzyme, characterized by
withdrawing a vaporous aqueous stream from the blow tank for maintaining the absolute pressure in said blow tank below atmospheric pressure.

Further, the present invention relates to a device for treating biomass comprising
a biomass feeding system;
a pressurized reactor for thermally treating the biomass;
a blow tank;
a discharging system for discharging the hydrolyzed biomass from the pressurized reactor to the blow tank by steam explosion; and
a unit for enzymatically treating a pumpable slurry stream of biomass discharged from the blow tank;

wherein
the blow tank comprises
    means for maintaining the absolute pressure in the blow tank below atmospheric pressure, preferably below 0.5 bar (a), still more preferably below 0.3 bar(a) and most preferably from 0.01 to 0.25 bar (a);
    at least one injection port for injecting an aqueous diluent;
    at least one discharge port for discharging said pumpable slurry stream of biomass;
    at least one discharge port for discharging a vaporous aqueous stream.

Definitions

Biomass is any source of plant material suitable for converting into pulp and paper material, cellulose-based construction material or biofuel. Suitable sources of biomass are lignocellulosic biomass such as virgin biomass, waste biomass and energy crops. Virgin biomass includes all naturally occurring terrestrial plants such as trees, bushes and grass. Waste biomass is produced as a low-value byproduct of various industrial sectors such as agriculture, e.g. selected from corn stover, sugarcane bagasse, straw etc., and forestry, e.g. selected from saw mill and paper mill discards. Energy crops are crops with high yield of lignocellulosic biomass produced to serve as a raw material for production of second generation (2G) biofuel. Examples include switch grass (Panicum virgatum) and elephant grass. In the present invention lignocellulosic biomass is used. The terms "lignocellulosic biomass" and "biomass" are used exchangeably.

DETAILED DESCRIPTION

Method

The present invention relates to a method for treating biomass comprising the steps of
(a) feeding lignocellulosic biomass to a pressurized reactor;
(b) supplying steam to the pressurized reactor and at least partially condensing said steam in the pressurized reactor;
(c) hydrolysing hemicellulose sugars of said biomass with said at least partially condensed steam in the pressurized reactor;
(d) discharging said hydrolyzed biomass from the pressurized reactor into a blow tank by steam explosion to produce steam exploded biomass;
(e) diluting the steam exploded biomass in the blow tank with an aqueous diluent to a pumpable slurry; discharging the pumpable slurry from the blow tank as discharged pumpable slurry stream;
(f) treating the discharged pumpable slurry stream with an enzyme, characterized by
withdrawing a vaporous aqueous stream from the blow tank for maintaining the absolute pressure in said blow tank below atmospheric pressure
Before feeding the biomass into the pressurized reactor the biomass can be pretreated by cutting and/or washing.

The biomass can additionally be pretreated by dilute acid hydrolysis by contacting with a dilute solution containing an external acidic catalyst, reinforced autohydrolysis by contacting with a dilute solution containing a recirculated acidic catalyst or autohydrolysis by contacting with water. The external or recirculated acidic catalyst is preferably selected from sulphuric acid, acetic acid or sulphur dioxide as gas or dissolved in water to sulphurous acid. These pretreatment measures are well known in the art.

In one embodiment the biomass fed into the pressurized reactor is preferably a solid dry material.

In another embodiment the biomass fed into the pressurized reactor is preferably an aqueous slurry of biomass.

The biomass is preferably fed into the pressurized reactor by means of a feeding system. The feeding system preferably comprises means for actively conveying the biomass into the pressurized reactor such as a screw feeder, e.g. a plug screw feeder optionally with a force feed screw feeding the plug screw feeder.

Suitable means for actively conveying the biomass into the pressurized reactor are known in the art.

The pressurized reactor can comprise one or more such as one or two reactors.

In one embodiment the pressurized reactor comprises more than one reactor such as two reactors. If the pressurized reactor comprises more than one reactor, e.g. an impregnation reactor and a hydrolysis reactor, the reactors are usually arranged in series. For example, biomass can be fed into an impregnation reactor and then be impregnated in the impregnation reactor. In the impregnation reactor the biomass is usually impregnated by dilute acid hydrolysis by contacting with a dilute solution containing an external acidic catalyst, reinforced autohydrolysis by contacting with a dilute solution containing a recirculated acidic catalyst or autohydrolysis by contacting with water. The external or recirculated acidic catalyst is preferably selected from sulphuric acid, acetic acid or sulphur dioxide as gas or dissolved in water to sulphurous acid. Afterwards, the biomass can be discharged from the impregnation reactor and fed to the subsequent respectively downstream hydrolysis reactor. The pressurized reactor can also comprise two or more hydrolysis reactors arranged in series and operating at same or different temperature and pressure.

In the hydrolysis reactor the biomass is thermally treated preferably in the presence of water under pressure, more preferably by heating with steam, to produce a thermally treated biomass. In particular, the biomass can be exposed to steam in the hydrolysis reactor, wherein the steam is fed into the hydrolysis reactor in addition to the biomass. By exposing the biomass to steam, the biomass is pressurized in the hydrolysis reactor, and the steam is at least partially condensed. In contact with said at least partially condensed steam the hemicellulose sugars of the biomass are hydrolyzed so that a hydrolyzed biomass is obtained in the hydrolysis reactor.

In another embodiment the pressurized reactor comprises only one reactor which suitably is a hydrolysis reactor. In said single hydrolysis reactor the biomass is thermally treated and hydrolyzed in the presence of at least partially condensed steam as discussed above. In one embodiment the biomass is additionally impregnated in said single hydrolysis reactor as discussed above.

It is preferred that the biomass is thermally treated in the pressurized reactor, preferably the hydrolysis reactor, at a pressure of 5 to 35 bar(a), more preferably 10 to 25 bar(a), and most preferably of 15 to 20 bar(a).

The thermally treated biomass in the pressurized reactor, preferably the hydrolysis reactor, is preferably heated to a temperature of from 120° C. to 250° C., preferably from 150° C. to 220° C. and most preferably from 170° C. to 215° C.

The hydrolysis reactor can be a vertical hydrolysis reactor or a horizontal hydrolysis reactor. Vertical and horizontal hydrolysis reactors are generally known in the art.

The residence time of the thermally treated biomass in the pressurized hydrolysis reactor unit is preferably in the range of from 1 to 30 minutes, more preferably from 3 to 15 minutes, and most preferably from 5 to 10 minutes.

The hydrolyzed biomass is discharged from the pressurized reactor, for example in a blow valve or restriction, which may have the shape of a hole, arranged downstream the pressurized reactor.

The hydrolyzed biomass is discharged through steam explosion. The steam explosion is defined as a rapid pressure decrease leading to a flashing of the steam. By means of steam explosion the fibers of the biomass disrupted to improve the accessibility of the carbohydrates, such as cellulose, for subsequent processes, such as enzymatic hydrolysis. Steam explosion is a technique well known in the art of biomass pretreatment.

Before being discharged from the pressurized reactor by steam explosion, the hydrolyzed biomass in the pressurized reactor preferably has a temperature of from 120° C. to 250° C., more preferably from 160° C. to 230° C. and most preferably from 180° C. to 220° C.

When discharging the hydrolyzed biomass through steam explosion the weight amount of the biomass in the discharged hydrolyzed biomass is preferably in the range of from 25 to 60 wt %, more preferably in the range of from 30 to 55 wt %, and most preferably in the range of from 40 to 55 wt %, based on the total weight of the discharged hydrolyzed biomass.

Steam explosion is especially effective for the pretreatment of agricultural residues and hardwood.

The hydrolyzed biomass is discharged from the pressurized reactor by steam explosion into a blow tank, wherein the absolute pressure in the blow tank is maintained below atmospheric pressure.

Preferably the absolute pressure in the blow tank is maintained below 0.5 bar(a), still more preferably below 0.3 bar(a) and most preferably from 0.01 to 0.25 bar(a). It is preferred that the absolute pressure in the blow tank is adjusted and maintained to a certain absolute pressure in dependence of the temperature, which shall be adjusted for the enzymatic hydrolysis. For example, for a temperature of 70° C. required in the enzymatic hydrolysis the pressure in the blow tank is adjusted and maintained at 0.3 bar (a), for a temperature of 50° C. required in the enzymatic hydrolysis the pressure in the blow tank is adjusted and maintained at 0.12 bar (a) or for a temperature of 32° C. required in the enzymatic hydrolysis the pressure in the blow tank is adjusted and maintained at 0.05 bar (a).

It is preferred that the hydrolyzed biomass is directly discharged from the pressurized hydrolysis reactor into the blow tank.

The discharge from the reactor which operates at high pressure into the blow tank is violent. Part of the moisture contained in the pores of the biomass will evaporate to steam due to the decreased pressure. The steam expands and breaks the biomass structure. Also, mechanical effects (impact, friction), caused by high velocity during the discharge contribute to disintegration of the biomass.

Evaporated water (blow steam) and steam exploded biomass are separated in the blow tank in two separate streams, a vaporous aqueous stream and an aqueous slurry comprising the steam exploded biomass.

It is preferred that the two streams are separated by means for separating a vaporous aqueous stream from a liquid (aqueous) stream, such as a cyclone. Said means for separating a vaporous aqueous stream from a liquid (aqueous) stream is preferably situated in proximity to the blow tank, more preferably at the top of the blow tank.

The vaporous aqueous stream usually comprises aqueous steam and volatile organic compounds, such as furfural, furfural derivatives, carboxylic acids, like acetic acid or formic acid, and methanol. The vaporous aqueous stream can additionally contain mineral acid species such as e.g. $SO_2$ or sulphurous acid or chlorine containing species, especially from optional acidic impregnation of the biomass in the pressurized reactor as discussed above.

The vaporous stream is withdrawn from the blow tank, preferably separately from the aqueous slurry stream comprising the steam exploded biomass, preferably through a separate discharge port. By means of withdrawing said vaporous aqueous stream from the blow tank the absolute pressure in said blow tank is maintained below atmospheric pressure. The withdrawn vaporous aqueous stream is preferably at least partly condensed in means for condensing a vaporous aqueous stream. The means for condensing a vaporous aqueous stream is preferably a condenser, such as a condensing scrubber, preferably equipped with a recycle cooler. Said means for condensing a vaporous aqueous stream is preferably used as direct heat exchanger for maintaining the pressure in the blow tank.

It is preferred that the pressure in the blow tank is maintained by means of a heat exchanger. The heat exchanger is preferably selected from an indirect heat exchanger, such as a tube and shell heat exchanger, or a direct heat exchanger, such as a condensing scrubber, preferably equipped with a recycle cooler.

In the means for condensing a vaporous aqueous stream the withdrawn vaporous aqueous stream is preferably separated into a vaporous stream comprising methanol and a condensed stream comprising furfural and carboxylic acids.

For obtaining a pumpable slurry of steam exploded biomass, the steam exploded biomass in the blow tank is diluted with an aqueous diluent.

Said aqueous diluent is preferably obtained from a process downstream of the method for treating biomass according to the invention. Aqueous streams from downstream processes, which are suitable as aqueous diluent are e.g. a wash filtrate from enzymatic treatment or a condensate from ethanol rectification.

Generally, the temperature of said aqueous diluent is not important. It is, however, preferred that the temperature of said aqueous diluent is higher than the temperature of the pumpable slurry in said blow tank. The high temperature of the aqueous diluent is possible due to the evaporative cooling of the steam exploded biomass in the blow tank. This allows to introduce aqueous streams from downstream processes of high temperature without need of further cooling steps of this aqueous diluent. The temperature of said aqueous diluent is preferably in the range of from 45° C. to 100° C., more preferably from 45° C. to 90° C. and most preferably from 45° C. to 80° C.

As discussed above, the absolute pressure in the blow tank is preferably adjusted and maintained to a certain absolute pressure in dependence of the temperature which shall be adjusted for the enzymatic hydrolysis. As a consequence the pumpable slurry stream comprising the steam exploded biomass discharged from the blow tank does not need to be further cooled before being treated with an enzyme.

In order to avoid further additional treatment steps of the pumpable slurry stream for optimizing the slurry for enzymatic treatment one or more additional streams can be introduced into the blow tank.

For adjusting the pH of the pumpable slurry stream an alkaline solution can be introduced into the blow tank.

Thereby, the pH of the pumpable slurry stream is preferably adjusted to 4.0 to 6.5. A pH of 4.0 to 6.5 usually is the optimum pH for enzymatic hydrolysis.

Further, an aqueous solution comprising enzymes for saccharification of cellulose can be introduced into the blow tank.

The pumpable slurry stream discharged from the blow tank preferably is in the condition to be directly treated with an enzyme in an enzymatic hydrolysis step. It is preferred that the pumpable slurry stream after discharge from the blow tank is not subjected to a further cooling step or to a further pH adjusting step or both before being treated with an enzyme.

The solids concentration in the pumpable slurry stream is preferably adjusted to 5 to 20 wt %, more preferably 10 to 20 wt %, and most preferably 15 to 20 wt %, based on the total weight of the pumpable slurry stream. It is preferred that the discharged pumpable slurry stream has a temperature of from 40 to 80° C., more preferably of 40 to 75° C. and most preferably of from 40 to 60° C. It is further preferred that the discharged pumpable slurry stream has a pH of 4.0 to 6.5.

It is additionally preferred that the discharged pumpable slurry stream has a solids concentration in the discharged pumpable slurry stream of from 5 to 20 wt %, more preferably of from 10 to 20 wt %, and most preferably of from 15 to 20 wt %, based on the total weight of the discharged pumpable slurry stream.

By enzymatic hydrolysis the carbohydrates such as cellulose in the biomass are hydrolyzed to mono- or oligosaccharides.

The method according to the invention is preferably operated in continuous mode.

Device

The present invention further relates to a device for treating biomass comprising
a biomass feeding system;
a pressurized reactor for thermally treating the biomass;
a blow tank;
a discharging system for discharging the hydrolyzed biomass from the pressurized reactor to the blow tank by steam explosion; and
a unit for enzymatically treating a pumpable slurry stream of biomass discharged from the blow tank;
wherein
the blow tank comprises
  means for maintaining the absolute pressure in the blow tank below atmospheric pressure, preferably below 0.5 bar (a), still more preferably below 0.3 bar(a) and most preferably from 0.01 to 0.25 bar (a);
  at least one injection port for injecting an aqueous diluent;
  at least one discharge port for discharging said pumpable slurry stream of biomass;
  at least one discharge port for discharging a vaporous aqueous stream.

The feeding system preferably comprises means for actively conveying the biomass into the pressurized reactor such as a screw feeder, e.g. a plug screw feeder optionally with a force feed screw feeding the plug screw feeder.

The pressurized reactor can comprise one or more such as one or two reactors. In one embodiment the pressurized reactor comprises more than one reactor such as two reactors, e.g. an impregnation reactor and a hydrolysis reactor.

In another embodiment the pressurized reactor comprises only one reactor which suitably is a hydrolysis reactor. The hydrolysis reactor can be a vertical hydrolysis reactor or a horizontal hydrolysis reactor.

For maintaining the reduced pressure in the blow tank, the blow tank preferably is a system which is closed up to the atmosphere.

The at least one injection port for injecting the aqueous diluent is preferably connected to a feeding line for the aqueous diluent from an apparatus unit further downstream of the blow tank to the blow tank. Said feeding line can connect the at least one injection port for injecting the aqueous diluent with e.g. enzymatic treatment unit or a unit for ethanol rectification.

Multiple injection port(s) can be situated over the whole length and width of the blow tank.

The blow tank further preferably comprises at least one, such as one or multiple, injection port(s) for injecting an alkaline solution in order to adjust the pH of the discharged thermally treated aqueous slurry of biomass is adjusted to 4.0 to 6.5.

Still further, the blow tank preferably comprises at least one, such as one or multiple, injection port(s) for injecting an aqueous solution comprising enzymes for saccharification of cellulose.

Multiple injection port(s) can be situated over the whole length and width of the blow tank.

The at least one discharge port for discharging aqueous slurry stream comprising the thermally treated biomass is preferably situated at the lower part of the blow tank.

The at least one discharge port for discharging the vaporous aqueous stream is preferably situated at the upper part of the blow tank.

It is preferred that the means for maintaining the absolute pressure in the blow tank below atmospheric pressure, preferably below 0.5 bar (a), still more preferably below 0.3 bar(a) and most preferably from 0.01 to 0.25 bar (a) comprises a heat exchanger. The heat exchanger is preferably selected from an indirect heat exchanger, such as a tube and shell heat exchanger, or a direct heat exchanger, such as a condensing scrubber, preferably equipped with a recycle cooler.

The blow tank preferably further comprises means for agitating the thermally treated aqueous slurry of biomass introduced into a blow tank, such as mixer, e.g. an axial mixer.

The vapor space in the blow tank is preferably at least 10 times the vapor space of the pressurized reactor.

Still further, the device of the invention preferably comprises means for separating a vaporous stream from a liquid (aqueous) stream in the blow tank, such as a cyclone. Said means for separating a vaporous stream from a liquid (aqueous) stream is preferably situated in proximity to the blow tank, more preferably at the top of the blow tank.

Additionally, the device preferably comprises means for condensing a vaporous stream. The means for condensing a vaporous stream is preferably a condenser, such as a steam condenser or a condensing scrubber, preferably equipped with a recycle cooler. Said means for condensing a vaporous stream is preferably used as direct heat exchanger for maintaining the pressure in the blow tank.

Still further, the device preferably comprises means for transporting the pumpable slurry stream of biomass from the blow tank to the unit for enzymatic treatment, such as a pump.

Benefits of the Invention

The present invention provides an improved method and device for treating biomass in which a cooling step for cooling the thermally treated and discharged biomass to the optimum temperature for enzymatic hydrolysation is omitted.

Additionally, the method and device of the present invention provide an efficient reduction of toxic compounds, like carboxylic acids or furfural, which reduce the activity of enzymes and yeast in the enzymatic hydrolysis.

Still further, an efficient liquid management is provided by the method and device of the present invention, which improves energy management, reduces waste streams and handles gases, all in an environmentally friendly manner.

DETAILED DESCRIPTION OF THE FIGURES

Figure 1:
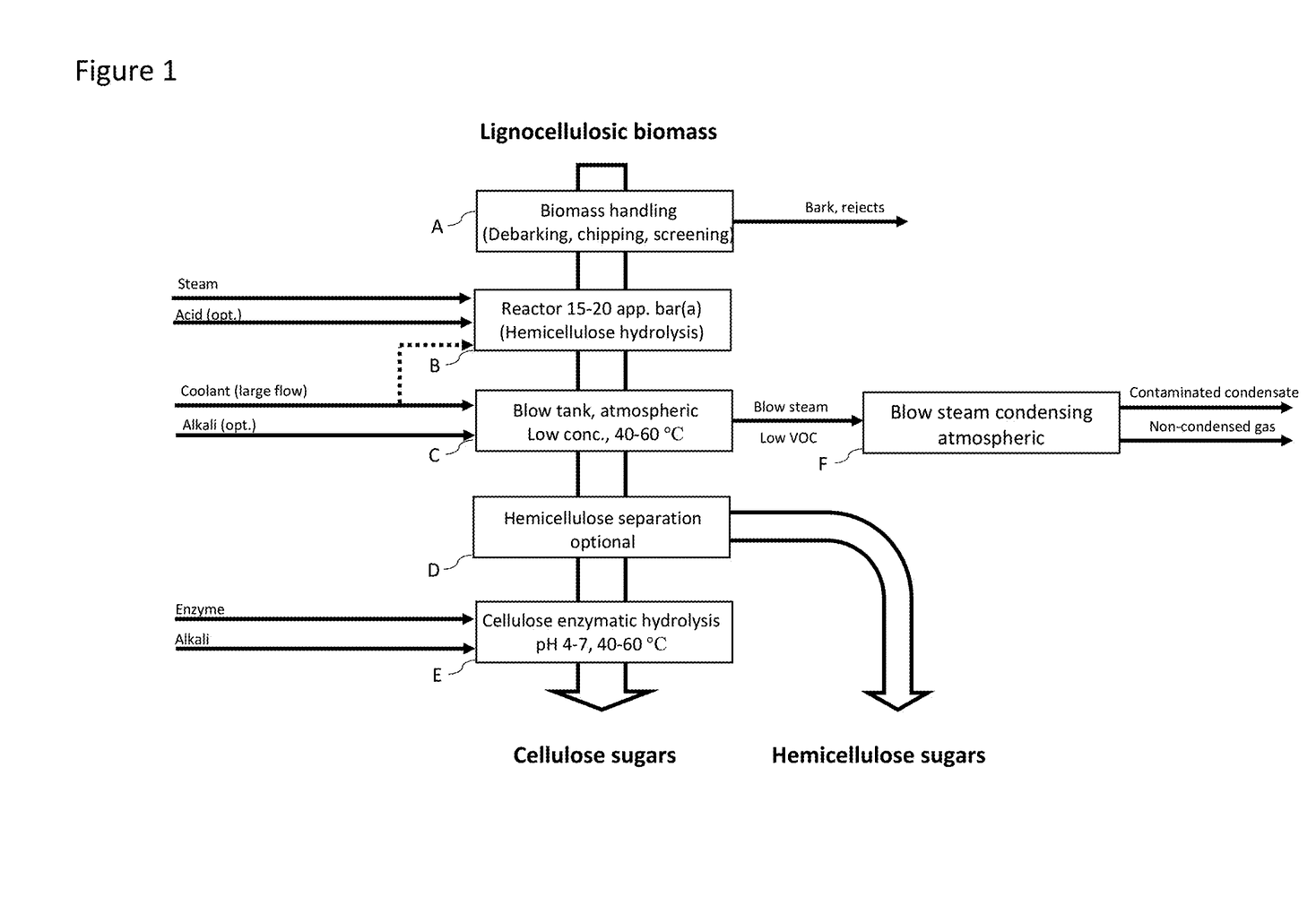
FIG. 1 exemplifies a typical biomass pre-hydrolysis process.

FIG. 1 exemplifies a typical biomass pre-hydrolysis process of the prior art. A lignocellulosic biomass of woody or agricultural origin is taken to a biomass handling step, A. The biomass is, if necessary de-barked, chipped or hammer-milled and screened for separation of harmful and inert solid material from biomass, for example gravel, stones metal particles and alike. Bark may also be separated as a reject. The biomass is then fed into the hydrolysis step B by means of a feeding system. The feeding system preferably comprises means for continuously conveying biomass into the reactor such as a screw feeder. The pressurized-hydrolysis step B may comprise one or multiple reactor shells connected in series or in parallel and they may be arranged vertically or horizontally. Vertical and horizontal hydrolysis reactors are generally known in the art. The biomass is heated in the reactor(s) with direct steam to the required process temperature and pressure. The temperature is typically 170-215° C. and the pressure in the range 10-25 bar. An acid may be added to step B to catalyze the hydrolysis reactions. The residence time of the biomass in the reactor unit is in the range of from 3 to 30 minutes. Hydrolyzed biomass is discharged, after completed hydrolysis reactions, through a blow valve or an orifice from the high pressure prevailing in the reactor to the atmospheric pressure prevailing in the blow tank, step C. The pressure-drop over the blow valve or orifice is high which results in efficient defibration of the biomass and opens the fiber structure making good access for enzymes in downstream hydrolysis steps. The temperature of the hydrolyzed biomass drops rapidly at the discharge as water and volatile material evaporate to the equilibrium temperature which is about 100° C. Such a discharge with a sudden pressure drop over a restriction is also called "steam explosion" discharge. Evaporated water, blow steam which also contains some volatile hydrocarbons, is evacuated from the blow tank to a condensing system, F. Condensed blow steam from step F is sent to a waste water treatment system and non-condensed gas to exhaust gas handling system. The hydrolyzed biomass which is discharged to the blow tank is around 100° C. which is too high for down-stream enzymatic hydrolysis and it is not pumpable. Enzymes typically works effectively in the temperature range 40-60° C. Known prior art proposes cooling and dilution of the biomass by mixing with an aqueous coolant. Such a dilution with a coolant may take place in the blow tank as indicated in FIG. 1 or in another container located downstream after the blow tank. In some cases, is coolant added upstream the blow valve or orifice (to step B). This is sometimes denoted "dilution discharge" since the liquid vaporization over the blow valve or orifice is reduced due to the cooling and dilution effect. The hydrolyzed slurry from step C, is pumped to step E for enzymatic hydrolysis. An optional step D, may be installed before step E. Dissolved hemicellulose sugars are washed in step D with a drum-washer, screw-press or alike and are treated separately from cellulose containing wet solid phase which is transported to said step C for enzymatic treatment. The solid phase is in such case diluted again to a consistency suitable for enzymatic hydrolysis. The process outlined is a continuous process, which means the feed of material to step B and the discharge of material from said step B are continuous, but variations exists where step B is operated as a batch process.

The draw-back of the process in FIG. 1 is that the dilution in step C (and step B if used), for achieving 40-60° C. slurry temperature, may be such that the consistency of the slurry is very low, resulting in a very high volumetric process (diluted slurry) flow. High volumetric flow will result in very large reactor (tank) sizes for enzymatic hydrolysis and fermentation. The diluted slurry also contains compounds, which are toxic and may be harmful for enzymes and yeast since the evaporative cooling to step C only reach 100° C.

Figure 2:
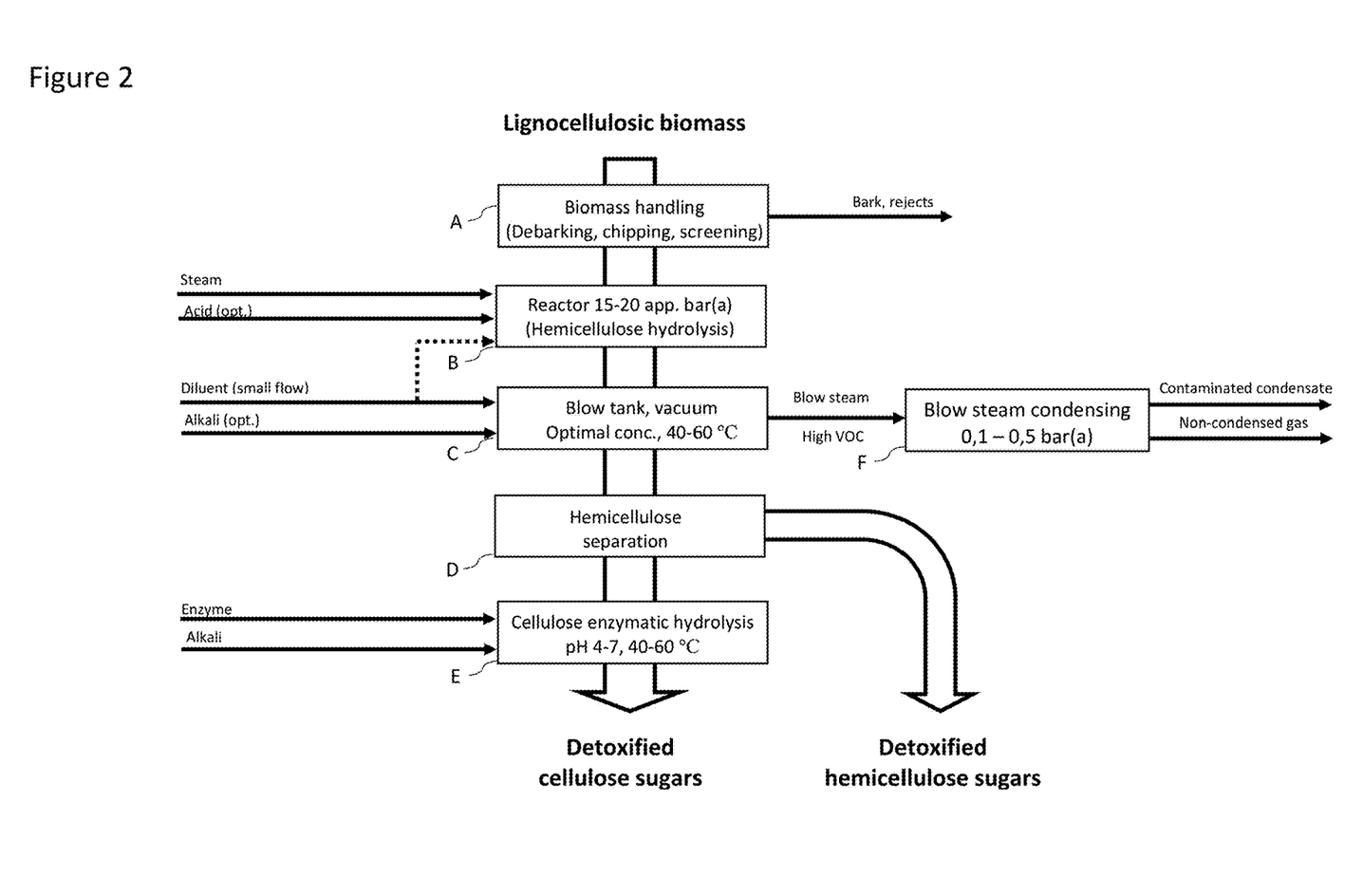
FIG. 2 shows a schematic overview of the method and device of the present invention.

FIG. 2 exemplifies schematically an embodiment of biomass hydrolysis according to the present invention. The difference to prior art, as exemplified in FIG. 1, is that the blow tank, step C, is sealed to atmospheric pressure and is operated under vacuum. The absolute pressure in the blow tank is below atmospheric pressure, preferably below 0.5 bar (a), still more preferably below 0.3 bar(a) and most preferably from 0.01 to 0.25 bar (a). Evaporative cooling in the blow tank may now proceed to 40-60° C. i.e. to a temperature which is favourable for enzymatic hydrolysis. The hydrolyzed biomass may be diluted in the blow tank to any required consistency independent of the required slurry temperature.

In other words, the present invention adds one more degree of freedom for optimising the conditions for enzymatic hydrolysis. The flow of diluent is optimized which will result in small reactor (tank) sizes for enzymatic hydrolysis and fermentation thus reducing investment costs. The evaporative cooling in step C is more extensive in comparison to prior art. Significantly more steam will evaporate from biomass thereby introducing a stripping effect which efficiently desorbs furfural, acetic acid, formic acid and other hydrocarbons alike to the vapour phase. The resulting slurry has a reduced content of these toxic compounds which results in better yield in downstream hydrolysis and fermentation.

The partial vaporisation of carboxylic acids results in a lower usage of alkali for pH adjustment as well. As said, an acid may be used in catalysing hydrolysis in step B. The catalyst may be a mineral acid but also $SO_2$ or sulphurous acid. The present invention will reduce the concentration of $SO_2$ or sulphurous acid in the slurry in the case such catalysts are used, thereby reducing the requirement of alkali for neutralization.

Figure 3:
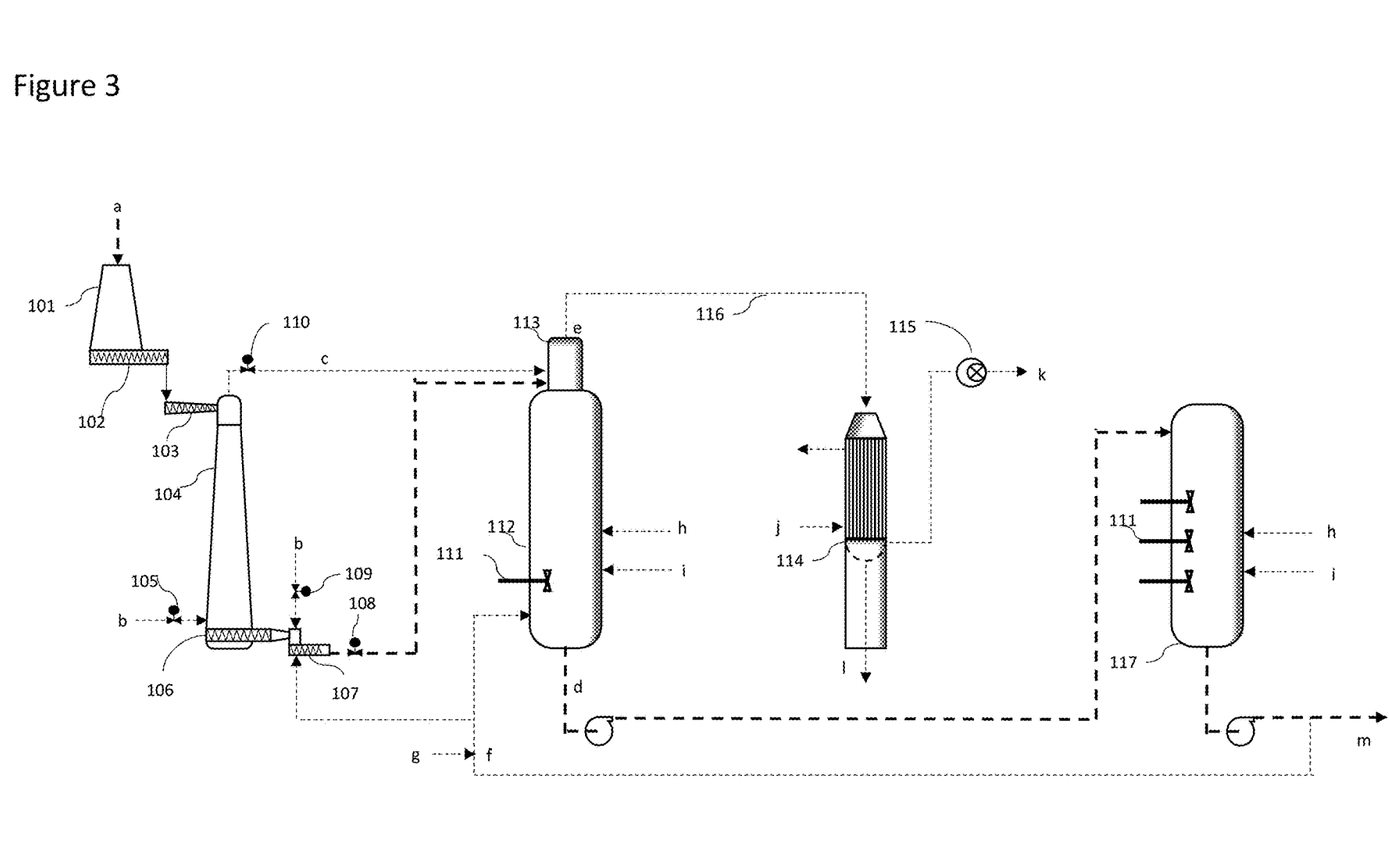
FIG. 3 shows a detailed example of biomass hydrolysis according to the present invention.

FIG. 3 shows a schematic overview of the method and device of the present invention. Lignocellulosic biomass (a), for example wood, bark, bagasse and straw, is fed to a receiving bin 101 which equalises variations in raw material flow and provides a sufficient volume for a stable material supply to the feeding screws 102 and 103. The raw material (a) to the bin 101 is split up to chips, flakes or splinters and it may be screened for removal of unwanted components such as sand or gravel which can cause wear and blockages in downstream machineries. The biomass is normally not dried, and it has a typical moisture content in the range of 30-50%. But, this not a limitation, the next process step, the thermal treatment step (steam explosion step) works well with dry material, down to approximately 10% of moisture but also with a material having a moisture above 50%. The bin 101 is operated at atmospheric pressure but the thermal treatment reactor 104 operates at elevated temperature, 170-215° C., and pressure, 10-25 bar(a). The screw 102, which is operated essentially at atmospheric pressure, provides a constant flow of biomass to the next screw, 103. Screw 103, also denoted "plug-screw", is conical and it compresses the biomass to a hard plug such that the high pressure in the reactor 104 is sealed to atmospheric pressure. Both screws work continuously and the hard pressure sealing biomass plug formed in screw 103 is mechanically disintegrated when it exits to the reactor 104. Steam (b), is added to the reactor for heating the and hydrolysing the biomass. Hemicelluloses of the biomass are easily hydrolyzed at the high temperature prevailing in the reactor forming sugar oligomers and monomers. A part of the sugars released will dehydrate to furfural and hydroxymethyl furfural which are unwanted in downstream fermentation processes. Also volatile by products are formed and released from the biomass, such as acetic acid, formic acid and methanol. Sulphuric acid or sulphurous acid may be added to the process for catalysing hydrolysis. The acid may be added directly to the biomass in the reactor 104, but it is possible to add it before the screw 103 in dedicated mixing screws or soaking systems (not shown in FIG. 3). Alternatively, sulphur dioxide gas may be added as catalyst, either to the reactor 104, but preferably to a mixing or soaking system upstream plug screw 103. Biomass containing hydrolysate is emptied from the reactor 104 with a screw and/or a scraper, 106 which is in the bottom. The biomass is discharged to a blow tank 112 through a blow valve with an adjustable aperture or a fixed orifice, 108. The blow tank, 112, is operated below atmospheric pressure (below 1.01 bar(a)). The pressure-drop over valve 108 is very high since the upstream pressure is 10-25 bar. The high pressure-drop over the valve results in a "steam explosion" by which is meant that water evaporates in the pores and cavities of the biomass when pressure rapidly decreases, thereby expanding and destroying the biomass material structure. The result of steam explosion is an open material structure suitable for down-stream enzymatic hydrolysis. A rotating mixer or screw, 107, may be installed upstream the blow valve 108, for assisting of the discharge of biomass through the blow valve or a discharge orifice. Further, steam (b) is added to said mixer, 107, for helping discharge of biomass through the blow valve. Hydrolyzed biomass is collected to the blow tank, 112 which is operated below the atmospheric pressure, 1.01 bar(a). The blow-tank is sealed to ambient atmosphere such that air cannot leak into it. Biomass and hydrolysate may be separated with cyclonic part, 113 installed at the top of the blow tank. The biomass inlet to the blow tank is tangential and the diameter of the top part is selected such that a high tangential velocity is reached for good separation of steam and biomass. The pressure in the blow tank is controlled with a blow steam condensing system including a condenser 114. Blow steam, (e), is a mixture of steam originating from the pre-treatment reactor 104 and steam obtained from water and volatile hydrocarbons which evaporate from moist hydrolyzed biomass. Blow steam (e) is conducted with a pipe 116 to the condenser 114. The blow steam condenser 114 is preferably a vertical tube and shell heat exchanger with the blow steam inside the tubes and a coolant (j) on the shell side. Blow steam condensate (l), contaminated with condensable hydrocarbons, is collected in the bottom part of the condenser and is pumped to other process steps for recovery of chemicals and/or effluent treatment system. The blow steam contains also non-condensable gases (k) which are evacuated from the condenser by means of a vacuum pump, 115, preferably a liquid ring pump. The chemicals contained in the non-condensable gas (k) may be recovered with an absorption tower or the gas is burned for example in a torch or a nearby boiler. The (total) pressure in the blow tank 112 is so low that the biomass is evaporatively cooled to a temperature which is suitable in down-stream enzymatic hydrolysis 117. For example, the pressure in the blow tank is adjusted to 12 kPa if 50° C. was required in the enzymatic step.

Most of the moisture in the biomass is water so the steam pressure is approximately follows that of pure water corrected with the boiling point elevation caused by dissolved hemicellulose sugars. The biomass is diluted to a pumpable slurry by mixing, for example hydrolysate (f) from downstream process steps 117 to the blow tank. Dilution liquid may be added also upstream the blow valve 107, if a "dilution blow" discharge is preferred. Dilution of biomass in/to the blow-tank may also be achieved by replacing recycle hydrolysate partly or wholly with a suitable recycle condensate and/or water (g). The temperature of the diluent is not important, it may be hot because it is still evaporatively cooled in the blow tank to the equilibrium temperature. This is one benefit of the invention as heat exchangers for diluent cooling are not required. Mixing in the blow tank may be assisted with wall mounted axial mixer(s), 111. Enzymes for hydrolysis of cellulose (h) may be added either to the blow tank or in the downstream enzymatic step(s) or both. In the same manner is acidity adjusted by adding a suitable caustic solution to blow tank 112 or to the coolant (g) or in enzymatic step(s) 117. As said above, the hydrolysis process in reactor 104 releases in parallel with hemicellulose sugar several components, some of which are unwanted in enzymatic hydrolysis and fermentations. According to the invention is biomass and hydrolysate from the reactor cooled evaporatively to a relatively low temperature. In known steam explosion processes biomass is cooled (evaporatively at pressure release) from for example 200° C. to 100° C., but according to the present invention evaporative cooling is performed from 200° C. to e.g. 50° C. The water evaporation thus increases by 50% in this example which results in more improved flash evaporation of (unwanted) hydrocarbon compounds. The hydrolysate from the blow tank 112 will be cleaner in comparison to prior art and this way will enzymatic hydrolysis downstream work better. Said detailed description is an example only and variations embracing the claims of the present invention may be outlined.

The invention claimed is:
1. A method comprising the steps of
(a) feeding lignocellulosic biomass to a pressurized reactor;
(b) supplying steam to the pressurized reactor and at least partially condensing said steam in the pressurized reactor;

(c) hydrolysing hemicellulose sugars of said biomass with said at least partially condensed steam in the pressurized reactor;
(d) discharging said hydrolyzed biomass from the pressurized reactor into a blow tank by steam explosion to produce steam exploded biomass;
(e) diluting the steam exploded biomass in the blow tank with an aqueous diluent to a pumpable slurry; discharging the pumpable slurry from the blow tank as discharged pumpable slurry stream; and withdrawing a vaporous aqueous stream from the blow tank for maintaining the absolute pressure in said blow tank below atmospheric pressure; and
(f) treating the discharged pumpable slurry stream with an enzyme.

2. The method of claim 1, wherein the absolute pressure in the blow tank is maintained below 0.5 bar(a).

3. The method of claim 2, wherein the absolute pressure in the blow tank is maintained below 0.3 bar(a).

4. The method of claim 2, wherein the absolute pressure in the blow tank is maintained at from 0.01 bar(a) to 0.25 bar(a).

5. The method of claim 1, wherein the aqueous diluent is obtained from a downstream process.

6. The method of claim 1, wherein the temperature of the aqueous diluent is higher than the temperature of the pumpable slurry in said blow tank.

7. The method of claim 1, wherein the pressure in the blow tank is maintained by means of a heat exchanger, which is selected from the group consisting of an indirect heat exchanger and a direct heat exchanger.

8. The method of claim 1, wherein the pH of the pumpable slurry is adjusted to 4.0 to 6.5 by introducing an alkaline solution into the blow tank.

9. The method of claim 1, wherein an aqueous solution comprising enzymes for saccharification of cellulose is introduced into the blow tank.

10. The method of claim 1, wherein the solids concentration in the pumpable slurry is adjusted to 10 wt % to 20 wt %, based on the total weight of the pumpable slurry.

11. The method of claim 1, wherein discharged pumpable slurry has a temperature of from 40° C. to 80° C.

12. The method of claim 1, wherein the vaporous aqueous stream withdrawn from the blow tank comprises water vapor, furfural, carboxylic acids and methanol.

13. The method of claim 1, wherein the hydrolyzed biomass in the pressurized reactor has a temperature of from 120° C. to 250° C. before being discharged by steam explosion into the blow tank.

14. The method of claim 7, wherein the heat exchanger is a tube and shell heat exchanger.

15. The method of claim 7, wherein the heat exchanger is a condensing scrubber.

16. The method of claim 15, wherein the condensing scrubber is equipped with a recycle cooler.

* * * * *